(12) United States Patent
Hsu

(10) Patent No.: US 9,254,344 B2
(45) Date of Patent: Feb. 9, 2016

(54) MOBILE POWER PACK WITH FRAGRANCE FEATURE

(71) Applicant: Powergene Technology Co., Ltd., Taiwan Branch, New Taipei (TW)

(72) Inventor: Hui-Te Hsu, New Taipei (TW)

(73) Assignee: POWERGENE TECHNOLOGY CO., LTD., TAIWAN BRANCH, New Taipei (TW)

( * ) Notice: Subject to any disclaimer, the term of this patent is extended or adjusted under 35 U.S.C. 154(b) by 36 days.

(21) Appl. No.: 14/315,689

(22) Filed: Jun. 26, 2014

(65) Prior Publication Data

US 2015/0374870 A1 Dec. 31, 2015

(51) Int. Cl.
| | | |
|---|---|---|
| *A01G 13/06* | (2006.01) | |
| *F24F 3/14* | (2006.01) | |
| *A61H 33/06* | (2006.01) | |
| *A61L 9/03* | (2006.01) | |

(52) U.S. Cl.
CPC .......................................... *A61L 9/03* (2013.01)

(58) Field of Classification Search
None
See application file for complete search history.

(56) References Cited

U.S. PATENT DOCUMENTS

| | | | | | |
|---|---|---|---|---|---|
| 3,603,765 | A * | 9/1971 | Underwood | ............. | A45D 4/16 132/229 |
| 4,849,606 | A * | 7/1989 | Martens, III | ....... | B65D 77/2024 239/34 |
| 5,067,169 | A * | 11/1991 | Chiu | ...................... | F24F 6/025 261/142 |
| 7,740,395 | B2 * | 6/2010 | Samuel | ..................... | A61L 9/03 362/101 |
| 8,068,725 | B2 * | 11/2011 | Cheung | ................... | A61L 9/037 392/386 |
| 8,090,244 | B2 * | 1/2012 | Belongia | ............. | A01M 1/2077 392/386 |
| 8,218,954 | B2 * | 7/2012 | Zuo | ........................... | A61L 9/03 392/386 |
| 8,752,545 | B2 * | 6/2014 | Buchberger | .......... | A24F 47/008 128/203.12 |
| 2004/0235430 | A1 * | 11/2004 | Ma | ............................. | A61L 9/03 455/90.1 |
| 2005/0175331 | A1 * | 8/2005 | Tam | ..................... | A01M 1/2072 392/405 |
| 2007/0237498 | A1 * | 10/2007 | Helf | ....................... | A01M 1/205 392/386 |
| 2008/0056691 | A1 * | 3/2008 | Wingo | ................. | A01M 1/2033 392/395 |
| 2010/0322599 | A1 * | 12/2010 | Landry | ..................... | A61L 9/03 392/386 |
| 2012/0325227 | A1 * | 12/2012 | Robinson | ............ | A61M 11/041 131/328 |
| 2014/0286630 | A1 * | 9/2014 | Buchberger | ........ | A61M 11/041 392/395 |
| 2015/0128967 | A1 * | 5/2015 | Robinson | .............. | A24F 47/008 131/328 |

* cited by examiner

*Primary Examiner* — Thor Campbell
(74) *Attorney, Agent, or Firm* — Chun-Ming Shih; HDLS IPR Services

(57) ABSTRACT

The present invention provides a mobile power pack with fragrance feature is disclosed. An outer surface of the housing is formed with an accommodating space, and a power module is installed in the housing. A heating element is disposed in the housing and corresponding to the accommodating space, and the heating element is electrically connected with the power module. A fragrant shim is disposed in the accommodating space, and the fragrant shim is heated by the heating element for producing aromas.

17 Claims, 3 Drawing Sheets

MOBILE POWER PACK WITH FRAGRANCE FEATURE

BACKGROUND OF THE INVENTION

1. Field of the Invention

The present invention generally relates to a mobile power pack and, in particular to a mobile power pack with fragrance feature.

2. Description of Prior Art

With the popularity of wireless communications and wireless networks, the frequency of using smart mobile devices is increased in daily life, but the consumption of electric power will be increased also. For this reason, most people will carry a mobile power pack for charging mobile device at anytime, in anywhere. A mobile power pack is a kind of portable charger of power supply and charging. Generally speaking, a mobile power pack has a lithium battery core as a power storage unit because it has characteristics of high capacity, multi-purpose, small size, long life, safe and reliability.

Furthermore, using aromatherapy is a common natural therapy for modern people lived in a stressful life. The aromatherapy is helpful for stress relieving and healthy improvement. However, aromatic devices usually need containers for holding essential oils, and a heating component for heating essential oils is also required. The fragrances of the essential oils can become small aromatic molecules and emit to the air after heating. Although the aromatherapy has been shown to prevent mental diseases and has effectiveness of health care, aromatic devices which have to be used in a fixed location that will cause great inconvenience for users. Thus how to facilitate aromatherapy and implement it in a mobile power pack is a motive of the present invention.

In view of the above drawbacks, the Inventor proposes the present invention based on his expert knowledge and elaborate researches in order to solve the problems of prior art.

SUMMARY OF THE INVENTION

Accordingly, an object of the present invention is to provide a mobile power pack, which a fragrant shim is provided in the housing, and the fragrant shim can produce aromas for users after the fragrant shim being heated by the heating element.

In order to achieve the object mentioned above, the present invention provides a mobile power pack with fragrance feature including a housing, a power module, a heating element and a fragrant shim. An outer surface of the housing is formed an accommodating space, and the power module is installed in the housing. The heating element is disposed in the housing and corresponding to the accommodating space, and the heating element is electrically connected with the power module. The fragrant shim is disposed in the accommodating space. The fragrant shim is adapted to produce aromas after being heated by the heating element.

Another object of the present invention is to provide a mobile power pack, which further including a magnetic induction switch and a magnetic element. The magnetic element is provided with the fragrant shim and corresponding to the magnetic induction switch. Whereby the magnetic induction switch will be actuated when a magnetic element is induced, and signals will be transmitted to the circuit board as an actuating mechanism of the heating element. Thus users can avoid burning when the heating switch being pushed unexpectedly, and that a safety mechanism will be achieved.

Comparing to the prior art, the mobile power pack with fragrance feature of the present invention has provided a fragrant shim and a heating element disposed in the housing. The fragrant shim is adapted to produce aromas after being heated by the heating element. Thereby users can relieve stress or improve ambient odor through aromatherapy at any time, in any place. Furthermore, a magnetic induction switch is provided in the housing, and the induction of the magnetic induction switch will be an actuating mechanism of the heating element. Thus users can avoid burning when the heating switch being pushed unexpectedly, and that a safety mechanism will be achieved.

BRIEF DESCRIPTION OF DRAWING

The features of the invention believed to be novel are set forth with particularity in the appended claims. The invention itself, however, may be best understood by reference to the following detailed description of the invention, which describes a number of exemplary embodiments of the invention, taken in conjunction with the accompanying drawings, in which:

DETAILED DESCRIPTION OF THE PREFERRED EMBODIMENTS

In cooperation with attached drawings, the technical contents and detailed description of the invention are described thereinafter according to a number of preferable embodiments, being not used to limit its executing scope. Any equivalent variation and modification made according to appended claims is all covered by the claims claimed by the present invention.

Figure 1:
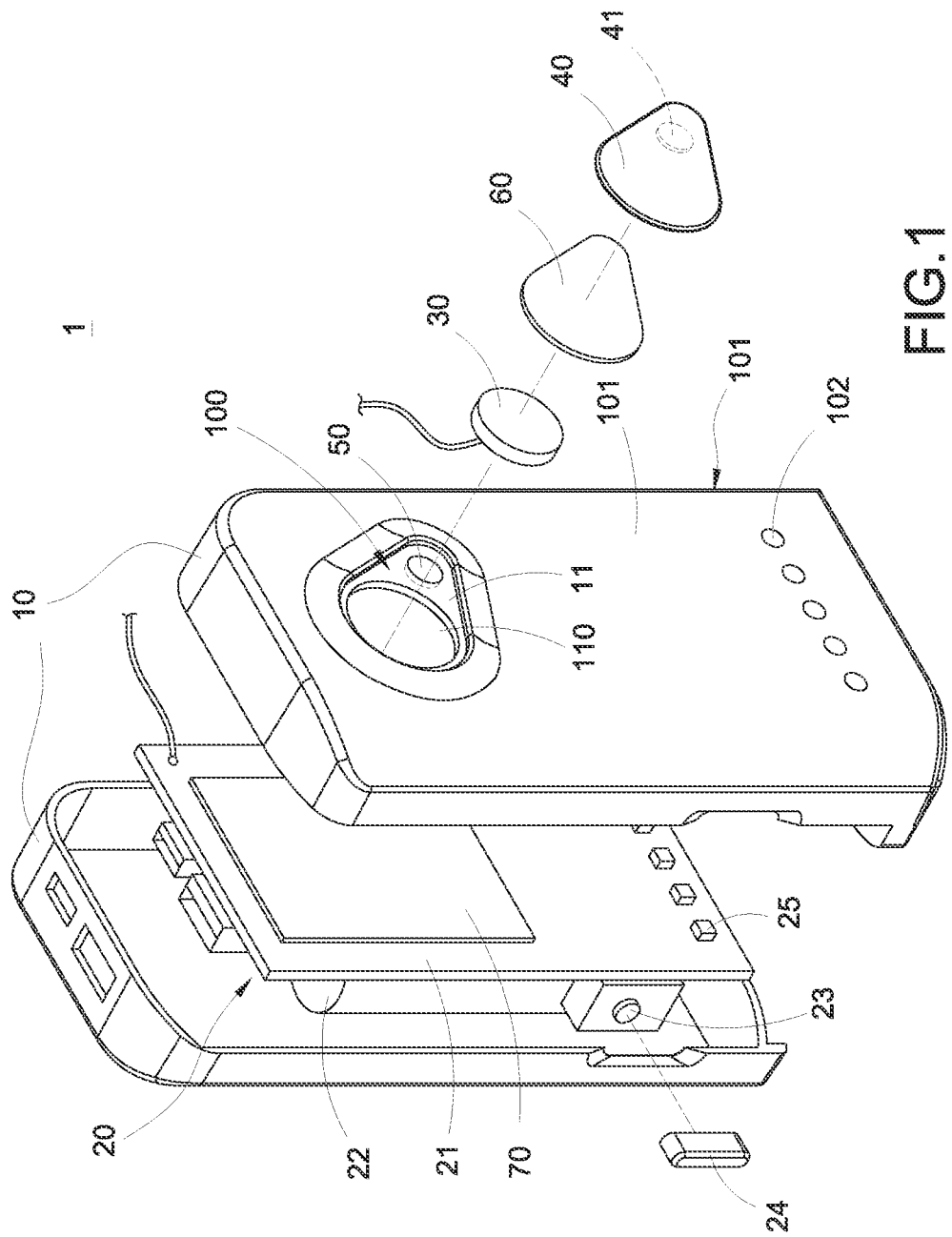
FIG. 1 is a perspective explosion schematic view of mobile power pack of the present invention.
Figure 2:
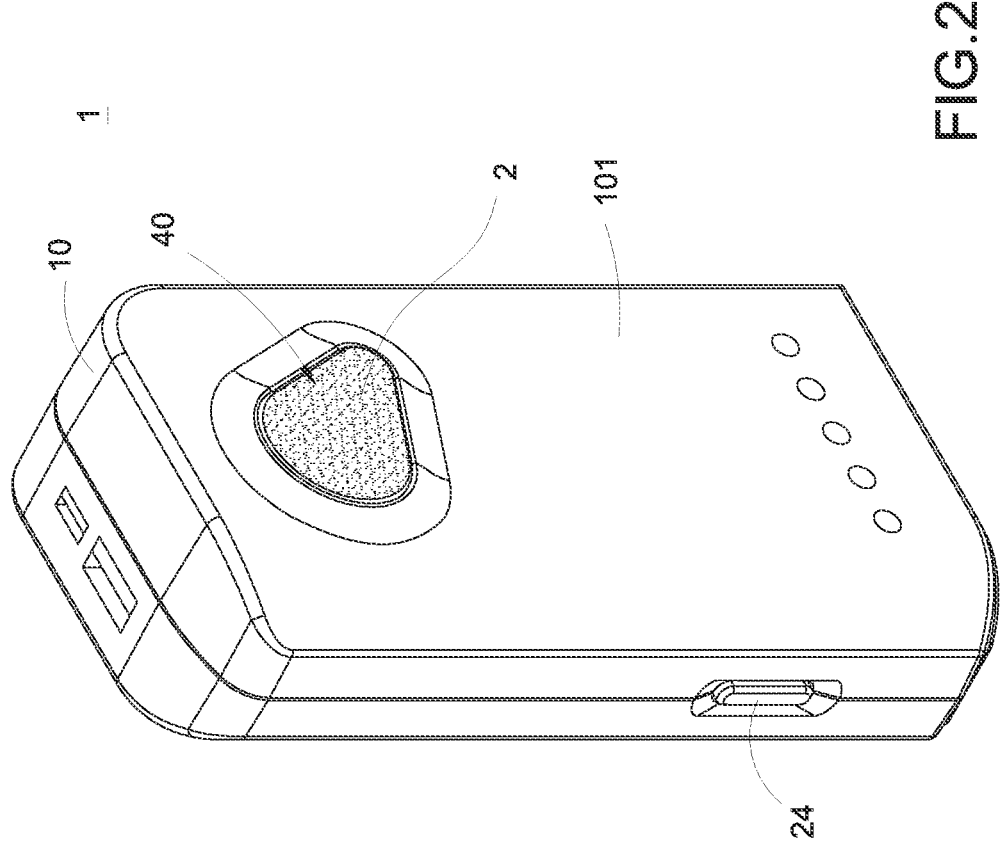
FIG. 2 is a perspective schematic view of mobile power pack of the present invention.
Figure 3:
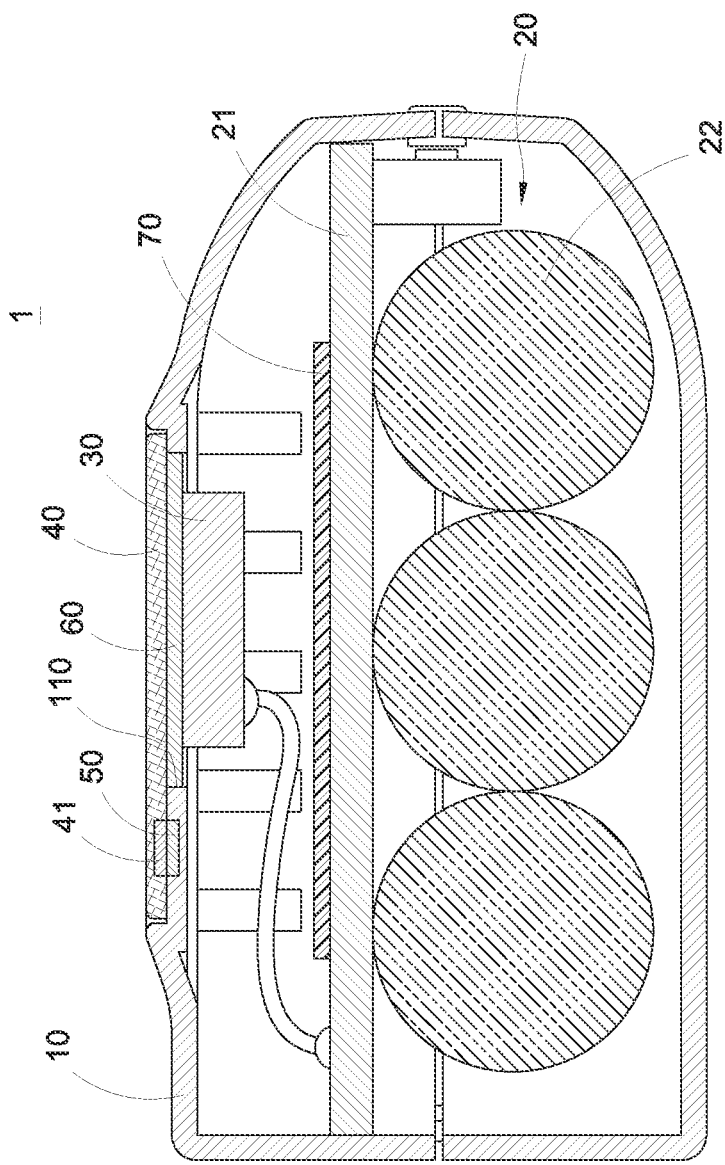
FIG. 3 is an assembly cross sectional view of mobile power pack of the present invention

Please refer to FIG. 1 to FIG. 3, they depict a perspective explosion schematic view and a perspective schematic view and an assembly cross sectional view of mobile power pack of the present invention. A mobile power pack 1 of the present invention includes a housing 10, a power module 20, a heating element 30 and a fragrant shim 40. The power module 20 and the heating element 30 are disposed in the housing 10, and the power module 20 provides the electricity for the heating element 30 generating the heat. The fragrant shim 40 has absorbed fragrances 2, and the fragrances 2 can be blended in a process of a shim for producing the fragrant shim 40, such as aromatic woods. In addition, users can drip flavoring, essential oils or other liquids on the fragrant shim 40 while making a fragrant shim 40.

The housing 10 has an outer surface 101, and the outer surface 101 has formed an accommodating space 100. In the present invention, the housing 10 further includes a partition 11 provided in the bottom of the accommodating space 100, and the fragrant shim 40 is placed on the partition 11.

The power module 20 is installed in the housing 10. In an embodiment of the present invention, the power module 20 includes a circuit board 21 and at least one rechargeable battery 22 electrically connected with the circuit board 21. The rechargeable battery 22 is, but not limited to, a lithium battery for recharging.

Moreover, the heating element 30 is electrically connected with the circuit board 21 of the power module 20. The pushing is disposed in the housing 10 and corresponding to the accommodating space 100. Besides, the heating element 30 can be, but not limited to, a mica electric heating plate or a ceramic heater. Preferably, the heating element 30 is located in the bottom of the accommodating space 100 for heating the fragrant shim 40 provided in the accommodating space 100.

The fragrant shim 40 is disposed in the accommodating space 100, and the fragrant shim 40 is heated by the heating element 30 for producing aromas. Furthermore, users can replace fragrant shim s 40 of different types based on personal likes.

In an embodiment of the present invention, the partition 11 of the housing 10 has an opening 110, and the heating element 30 will be exposed out of the opening 110 after disposing in the housing 10 (as shown in FIG. 3). Moreover, the power module 20 further includes a heating switch 23 electrically connected with the circuit board 21. A button 24 is operable to press against the heating switch 23, and the button 24 is partially exposed out of the housing 10. In addition, the power module 20 further includes at least one LED (light emitting diode) 25 electrically connected with the circuit board 21, and the housing 10 has at least one aperture 102 corresponding to the position of the LED 25.

In real practice, the mobile power pack 1 with fragrance feature of the present invention further includes a magnetic induction switch 50 and a heat conducting plate 60. The magnetic induction switch 50 is, but not limited to, a reed switch or an electromagnetic switch. The magnetic induction switch 50 is electrically connected with the circuit board 21 of the power module 20, and the magnetic induction switch 50 will transmit signals to the circuit board 21 when the magnetic induction switch 50 is actuated by an external force. In the present embodiment, the magnetic induction switch 50 is disposed in the housing 10 and corresponding to the accommodating space 100. For example, the magnetic induction switch 50 is assembled to a lateral side of the partition 11 and away from the accommodating space 100.

It is worth of notice that if the mobile power pack 1 with fragrance feature of the present has provided with the magnetic induction switch 50, the fragrant shim 40 should provide with a magnetic element 41 with respect to the magnetic induction switch 50. The magnetic element 41 will be attracted by the magnetic induction switch 50 because of a magnetic induction. The fragrant shim 40 will be positioned in the accommodating space 100 by the magnetic induction of the induction switch 50. Besides, the magnetic induction switch 50 will be actuated when a magnetic element 41 is induced, and signals will be transmitted to the circuit board 21. When the circuit board 21 receives the signals, the circuit board 21 will command the heating element 30 to work after the heating switch 23 being pushed. Thus users can avoid burning when the heating switch being pushed unexpectedly, and that a safety mechanism will be achieved.

Furthermore, the heat conducting plate 60 is disposed between the heating element 30 and the fragrant shim 40. The heat conducting plate 60 is provided for evenly transferring the heat of the heating element 30.

When using the mobile power pack 1 with fragrance feature of the present invention, the fragrant shim 40 should be placed in the accommodating space 100 firstly, and then the magnetic induction switch 50 (if provided) will be induced. After that, the button 24 can be pushed for starting the heating switch 2. At last, the heating element 30 starts to heat and the fragrant shim 40 will produce aromas after being heated.

Although the present invention has been described with reference to the preferred embodiment thereof, it will be understood that the invention is not limited to the details thereof. Various substitutions and improvements have been suggested in the foregoing description, and others will occur to those of ordinary skill in the art. Therefore, all such substitutions and improvements are intended to be embraced within the scope of the invention as defined in the appended claims.

What is claimed is:

1. A mobile power pack with fragrance feature, comprising:
    a housing having an outer surface, and the outer surface forming an accommodating space;
    a power module installed in the housing;
    a heating element disposed in the housing and corresponding to the accommodating space, the heating element being electrically connected with the power module;
    a fragrant shim disposed in the accommodating space, the fragrant shim adapted to produce aromas after being heated by the heating element; and
    a magnetic induction switch, wherein the magnetic induction switch is disposed in the housing and corresponding to the accommodating space, the magnetic induction switch is electrically connected with the power module;
    wherein the magnetic induction switch is assembled to a lateral side of the partition and away from the accommodating space.

2. The mobile power pack according to claim 1, wherein the housing further includes a partition provided in the bottom of the accommodating space, and the fragrant shim is placed on the partition.

3. The mobile power pack according to claim 2, wherein the partition has an opening and the heating element is exposed out of the opening.

4. The mobile power pack according to claim 1, wherein the fragrant shim has provided with a magnetic element with respect to the magnetic induction switch, and the fragrant shim is positioned in the accommodating space through the magnetic element inducted by the magnetic induction of the magnetic induction switch.

5. The mobile power pack according to claim 1, further including a heat conducting plate, and the heat conducting plate is disposed between the heating element and the fragrant shim.

6. The mobile power pack according to claim 1, further including a heat insulation film, and the heat insulation film is disposed between the heating element and the power module.

7. The mobile power pack according to claim 1, wherein the power module further includes a circuit board and at least one rechargeable battery electrically connected with the circuit board, and the heating element is electrically connected with the circuit board.

8. The mobile power pack according to claim 7, wherein the power module further includes a heating switch electrically connected with the circuit board and a button operable to press against the heating switch, and the button is partially exposed out of the housing.

9. The mobile power pack according to claim 7, wherein the power module further includes at least one light emitting diode (LED) electrically connected with the circuit board, the housing has at least one aperture corresponding to the position of the LED.

10. The mobile power pack according to claim 1, wherein the housing further includes a partition provided in the bottom of the accommodating space, and the fragrant shim is placed on the partition.

11. The mobile power pack according to claim 10, wherein the partition has an opening and the heating element is exposed out of the opening.

12. A mobile power pack with fragrance feature, comprising:
- a housing having an outer surface, and the outer surface forming an accommodating space;
- a power module installed in the housing;
- a heating element disposed in the housing and corresponding to the accommodating space, the heating element being electrically connected with the power module;
- a fragrant shim disposed in the accommodating space, the fragrant shim adapted to produce aromas after being heated by the heating element; and
- a magnetic induction switch, wherein the magnetic induction switch is disposed in the housing and corresponding to the accommodating space, the magnetic induction switch is electrically connected with the power module;
- wherein the fragrant shim has provided with a magnetic element with respect to the magnetic induction switch, and the fragrant shim is positioned in the accommodating space through the magnetic element inducted by the magnetic induction of the magnetic induction switch.

13. The mobile power pack according to claim 12, further including a heat conducting plate, and the heat conducting plate is disposed between the heating element and the fragrant shim.

14. The mobile power pack according to claim 12, further including a heat insulation film, and the heat insulation film is disposed between the heating element and the power module.

15. The mobile power pack according to claim 12, wherein the power module further includes a circuit board and at least one rechargeable battery electrically connected with the circuit board, and the heating element is electrically connected with the circuit board.

16. The mobile power pack according to claim 15, wherein the power module further includes a heating switch electrically connected with the circuit board and a button operable to press against the heating switch, and the button is partially exposed out of the housing.

17. The mobile power pack according to claim 15, wherein the power module further includes at least one light emitting diode (LED) electrically connected with the circuit board, the housing has at least one aperture corresponding to the position of the LED.

* * * * *